(12) United States Patent
Bandi et al.

(10) Patent No.: US 9,295,631 B2
(45) Date of Patent: Mar. 29, 2016

(54) SKIN LIGHTENING COMPOSITION

(71) Applicant: Conopco, Inc., Englewood Cliffs, NJ (US)

(72) Inventors: Babu Rakesh Kumar Bandi, Asansol (IN); Amit Chakrabortty, London (GB); Ganesh Chandramowli, Bangalore (IN); Anita Damodaran, Bangalore (IN); Marie Juliet, Bangalore (IN); Nirmala Nair, Bangalore (IN); Subarna Saha, Bangalore (IN); Shilpa Atul Vora, Bangalore (IN)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

(21) Appl. No.: 14/376,938

(22) PCT Filed: Feb. 5, 2013

(86) PCT No.: PCT/EP2013/052211
§ 371 (c)(1),
(2) Date: Aug. 6, 2014

(87) PCT Pub. No.: WO2013/120726
PCT Pub. Date: Aug. 22, 2013

(65) Prior Publication Data
US 2015/0157547 A1 Jun. 11, 2015

(30) Foreign Application Priority Data

Feb. 13, 2012 (IN) .......................... 390/MUM/2012
Apr. 10, 2012 (EP) .................................... 12163547

(51) Int. Cl.
*A61K 48/00* (2006.01)
*C07H 21/02* (2006.01)
*C07H 21/04* (2006.01)
*A61K 8/73* (2006.01)
*A61K 8/60* (2006.01)
*A61Q 19/02* (2006.01)
*C12N 15/113* (2010.01)

(52) U.S. Cl.
CPC . *A61K 8/73* (2013.01); *A61K 8/606* (2013.01); *A61Q 19/02* (2013.01); *C12N 15/113* (2013.01); *C12N 2310/14* (2013.01)

(58) Field of Classification Search
CPC .... A61K 48/00; C12N 15/113; C12N 15/111; C12N 2310/11
See application file for complete search history.

(56) References Cited

U.S. PATENT DOCUMENTS

| | | | |
|---|---|---|---|
| 7,087,743 | B2 | 8/2006 | Kurfurst |
| 7,504,385 | B2 | 3/2009 | Binetti |
| 7,999,096 | B2 | 8/2011 | Schmitt-Milas |
| 8,410,260 | B2 | 4/2013 | Collin-Djangone |
| 8,669,238 | B2 | 3/2014 | Raposo |
| 2005/0245475 | A1 | 11/2005 | Khvorova |
| 2007/0134188 | A1 | 6/2007 | Collin-Djangone |
| 2009/0202458 | A1 | 8/2009 | Binetti |
| 2010/0319074 | A1 | 12/2010 | Lu |
| 2012/0321575 | A1 | 12/2012 | Raposo |

FOREIGN PATENT DOCUMENTS

| | | |
|---|---|---|
| EP | 1752536 A1 | 2/2007 |
| EP | 2213738 A2 | 8/2010 |
| FR | 2890859 B1 | 3/2007 |
| FR | 2894582 | 6/2007 |
| FR | 2930151 | 10/2009 |
| FR | 2930152 | 10/2009 |
| GB | 2420119 | 5/2006 |
| JP | 8140699 | 6/1996 |
| WO | WO9731012 | 8/1997 |
| WO | WO2009001359 A2 | 12/2008 |
| WO | WO2010000901 | 1/2010 |
| WO | WO2010000901 A1 | 1/2010 |
| WO | WO2010080452 | 7/2010 |

OTHER PUBLICATIONS

Wu et al., "Mir-434-5p mediates skin whitening and lightening", Clinical Cosmetic and Invesitgational Dermatology, 2008, vol. 1, pp. 19-35.
Murase et al., "The Essential Role of p53 in Hyperpigmentation of the Skin via Regulation of Paracrine Melanogenic Cytokine Receptor Signaling", The Journal of Biological Chemistry, 2009, vol. 284, No. 7, pp. 4343-4353.
PCT International Search Report in PCT application PCT/EP2013/05221 dated Mar. 20, 2014 with Written Opinion.
European Search Report in EP application EP 12 16 3547 dated Nov. 20, 2012 with Written Opinion.
IPRP1 in PCTEP2013052211, Aug. 19, 2014.

*Primary Examiner* — Amy Bowman
(74) *Attorney, Agent, or Firm* — Greenberg Traurig, LLP

(57) ABSTRACT

The present invention relates to a skin lightening composition and a method of lightening skin. The skin lightening is achieved using siRNA oligonucleotides which are able to achieve this using much lower concentration as compared to known chemical actives.

4 Claims, No Drawings

SKIN LIGHTENING COMPOSITION

TECHNICAL FIELD

The present invention relates to a skin lightening composition and a method of lightening skin.

BACKGROUND OF THE INVENTION

Many skin lightening methods and compositions have been reported. Actives which are known for skin lightening can be prepared synthetically or may be used or extracted from natural sources. These actives can be used for skin lightening in general and also to treat, prevent or improve appearance of skin against hyperpigmentation, age spots, blemishes etc.

Skin color is determined by the amount, type and distribution of melanin within the epidermal cells. Keratinocytes are the major cells in the skin epidermis (>90% of the population) while fibroblasts are situated in the dermis and melanocytes (~5% of the total epidermal cells) are present at the dermal: epidermal junction. These three types of cells communicate with each other through various secreted factors to regulate skin pigmentation.

Melanocytes in skin synthesize melanin (a biopolymeric pigment) and transfer it to neighbouring keratinocytes, for distribution of melanin within the upper layers of the skin. Melanin is synthesized inside specialized lysosome-related organelles, termed melanosomes. Skin color is influenced by several factors including (a) the amount and types of melanin produced and transferred to keratinocytes and (b) its subsequent incorporation, aggregation and degradation within keratinocytes. Other factors that regulate skin pigmentation include factors secreted from keratinocytes and fibroblasts that affect melanocytes, endocrine factors from the blood supply, as well as neural factors and inflammation-related factors; extrinsic factors that affect skin pigmentation include ultraviolet (UV) radiation. Regulating some of these factors using siRNA have been reported.

siRNA are short double stranded small interfering RNA molecules. Most of the siRNA are 20-25 nucleotides in length. siRNA are involved in RNA interference and regulate (interfere with—silence) gene expression, post-transcriptionally. Synthetic siRNA can be introduced into cells using appropriate transfection procedures and typically demonstrate transient effects. This results in sequence complementarity based knock down of the corresponding target gene's expression. The above mentioned characteristic length seems to maximize target gene specificity over non-specific effects. When a particular target gene is known, the overall process includes selective design of a few siRNA sequences to target various parts of that gene and test out experimentally, to identify the most efficacious siRNA sequence(s) within that set (highest suppression of gene expression). The relevance of a given gene vis-à-vis a particular cellular phenomenon can be tested out using siRNA against that gene. siRNA thus serves both as an examination tool in the study gene function as well as a technology handle to modulate gene expression and through that, cellular physiology.

Oligonucleotides have been disclosed for depigmentation of skin e.g. in U.S. Pat. No. 7,087,743, U.S. Pat. No. 7,504,385, and US 2007/0134188. The oligonucleotides claimed in the present invention have not been disclosed in the above publications or any other published document for inclusion in a composition for application on skin.

A very large number of siRNA molecules for gene expression inhibition have been reported in EP1752536, EP2213738, WO2009/001359, and WO2010/080452 with possible use in pharmaceutical applications. However, none of them teach or direct one to use any of those oligonucleotides for application on skin for skin lightening benefit.

It is thus an object of the present invention to provide for novel oligonucleotides that provide enhanced skin lightening efficacy.

SUMMARY OF THE INVENTION

According to the first aspect of the present invention there is provided a skin lightening composition comprising an siRNA comprising
(a) an oligonucleotide comprising a sequence selected from one of

| | |
|---|---|
| UCAAUGACCACAUAGAUAAGGUCUC; | SEQ ID: 1 |
| UACUCAUUAGUACUAUCGCUGCAGG; | SEQ ID: 2 |
| UUAGAAUCAUUCUUGAUGUCUCUGG; | SEQ ID: 3 |
| UAACAGCCGGACAAGAAGAUGAUGG; | SEQ ID: 4 |
| AAGAGGUUGAAGUUCUUGAAGAUGC; | SEQ ID: 5 |
| CAAUUCACCCACACUGUTC; | SEQ ID: 6 |
| UUUAUUAAAGAUGCCACGUGG; | SEQ ID: 7 |
| UAGAAUCCCACCUUUACUCTG; | SEQ ID: 10 | or
a portion comprising at least 19 nucleotides thereof; and
(b) a cosmetically acceptable vehicle;
wherein the oligonucleotide size is from 19 to 30 nucleotides.

According to another aspect of the present invention there is provided a skin lightening composition comprising:
(a) an siRNA comprising an oligonucleotide comprising a sequence selected from the group consisting of

| | |
|---|---|
| CAAUUCACCCACACUGUTC; | SEQ ID: 6 |
| GUUCAUGAUGCCAAAGGCCTG; | SEQ ID: 8 |
| UUCAUUGCUGUGAUCAUUCGC; | SEQ ID: 9 | and
a portion comprising at least 19 nucleotides thereof; and
(b) a cosmetically acceptable vehicle selected from an emulsion, lotion, cream, foam, gel, soap bar, stick, mask, pad or patch;
wherein the oligonucleotide size is from 19 to 30 nucleotides According to another aspect of the present invention there is provided a method of lightening skin comprising applying to the skin, a composition of the invention.

DETAILED DESCRIPTION OF THE INVENTION

These and other aspects, features and advantages will become apparent to those of ordinary skill in the art from a reading of the following detailed description and the appended claims. For the avoidance of doubt, any feature of one aspect of the present invention may be utilized in any other aspect of the invention. The word "comprising" is intended to mean "including" but not necessarily "consisting of" or "composed of." In other words, the listed steps or options need not be exhaustive. It is noted that the examples given in the description below are intended to clarify the invention and are not intended to limit the invention to those examples per se. Similarly, all percentages are weight/weight percentages unless otherwise indicated. Except in the operating and comparative examples, or where otherwise explicitly indicated, all numbers in this description and claims indicating amounts of material or conditions of reaction, physical properties of materials and/or use are to be understood as modified by the word "about". Numerical ranges expressed in the format "from x to y" are understood to include x and y. When for a specific feature multiple preferred ranges are described in the format "from x to y", it is understood that all ranges combining the different endpoints are also contemplated.

By "Skin lightening composition" as used herein, is meant to include a composition for topical application to the skin to lighten the natural colour of the skin. Such a composition may be generally classified as leave-on or rinse off, and includes any product applied to a human body for also improving appearance, cleansing, odor control or general aesthetics. The composition of the present invention can be in the form of a liquid, lotion, cream, foam, scrub, gel, soap bar or toner, or applied with an implement or via a face mask, pad or patch. Non-limiting examples of such compositions include leave-on skin lotions, creams, antiperspirants, deodorants, foundations and wash-off shampoos, conditioners, shower gels, and toilet bars. The composition of the present invention is preferably a leave-on composition. "Skin" as used herein is meant to include skin on the face and body (e.g., neck, chest, back, arms, underarms, hands, legs, buttocks and scalp) and especially to the sun exposed parts thereof.

The composition of the invention comprises an siRNA (double stranded nucleotide) comprising select oligonucleotide of 19 to 30 nucleotides long formulated in a cosmetically acceptable base for skin lightening application. The oligonucleotides for use in the present invention are selected after extensive research in this area, the process of selection is described below.

The keratinocytes, melanocytes and fibroblasts present in skin communicate with each other through various secreted factors to regulate skin pigmentation. The present inventors have worked on a few of these factors, carefully shortlisted to maximize their influence on melanogenesis viz. Stem cell factor (SCF), Endothelin (EDN), α-melanocyte stimulating hormone (α-MSH) and Wnt which bind to their cognate receptors c-Kit Tyrosine kinase, Endothelin receptor A and B (EDNRA and EDNRB), Melanocortin 1 and Frizzled 1 (Fz1) respectively. Such interactions trigger multiple downstream signaling pathways which regulate skin pigmentation. The present inventors have analysed nucleic acid sequences which are most likely to suppress the receptors at the gene expression level and arrived at a large number of such sequences which are likely to regulate skin lightening. These large number of oligonucleotide sequences (present in double stranded siRNA) were then experimentally tested using melanin content in-vitro assay for their potential as skin lightening agents and arrived at the present invention which includes use of ten such oligonucleotides for providing skin lightening benefits.

The ten oligonucleotides are:

UCAAUGACCACAUAGAUAAGGUCUC; SEQ ID: 1

UACUCAUUAGUACUAUCGCUGCAGG; SEQ ID: 2

UUAGAAUCAUUCUUGAUGUCUCUGG; SEQ ID: 3

UAACAGCCGGACAAGAAGAUGAUGG; SEQ ID: 4

AAGAGGUUGAAGUUCUUGAAGAUGC; SEQ ID: 5

CAAUUCACCCACACUGUTC; SEQ ID: 6

UUUAUUAAAGAUGCCACGUGG; SEQ ID: 7

GUUCAUGAUGCCAAAGGCCTG; SEQ ID: 8

UUCAUUGCUGUGAUCAUUCGC; SEQ ID: 9
or

UAGAAUCCCACCUUUACUCTG; SEQ ID: 10 or
a portion comprising at least 19 nucleotides thereof.

According to a preferred aspect the portion comprising at least 19 nucleotides are contiguous nucleotides.

As per the present invention, oligonucleotide size is from 19 to 30 nucleotides long. The siRNA that works to provide the benefits of the invention can be as small as 19 nucleotides long and in such cases the desired nucleotide may be any portion of the sequences (1) to (10) claimed in the present invention. Alternately the desired oligonucleotide may be as long as 30 nucleotides long that comprises any one of the ten sequences in its entirety additionally comprising a few nucleotides attached at one or both ends.

According to a preferred aspect of the present invention the oligonucleotides are at least 20 nucleotides long, preferably at least 22 more preferably at least 25 nucleotides long. According to yet another preferred aspect the oligonucleotides are at the most 30, more preferably at the most 27, further more preferably at the most 25 nucleotides long. Most preferably the oligonucleotides are 19 to 25 nucleotide long. According to yet another preferred aspect of the present invention, the oligonucleotides are selected from

UCAAUGACCACAUAGAUAAGGUCUC; SEQ ID: 1

UACUCAUUAGUACUAUCGCUGCAGG; SEQ ID: 2

UUAGAAUCAUUCUUGAUGUCUCUGG; SEQ ID: 3

UAACAGCCGGACAAGAAGAUGAUGG; SEQ ID: 4

AAGAGGUUGAAGUUCUUGAAGAUGC; SEQ ID: 5

CAAUUCACCCACACUGUTC; SEQ ID: 6

-continued

UUUAUUAAAGAUGCCACGUGG;   SEQ ID: 7

GUUCAUGAUGCCAAAGGCCTG;   SEQ ID: 8

UUCAUUGCUGUGAUCAUUCGC;   SEQ ID: 9 or

UAGAAUCCCACCUUUACUCTG   SEQ ID: 10

The oligonucleotide is preferably one of

UCAAUGACCACAUAGAUAAGGUCUC;   SEQ ID: 1

UACUCAUUAGUACUAUCGCUGCAGG;   SEQ ID: 2

UUAGAAUCAUUCUUGAUGUCUCUGG;   SEQ ID: 3

UAACAGCCGGACAAGAAGAUGAUGG;   SEQ ID: 4

AAGAGGUUGAAGUUCUUGAAGAUGC   SEQ ID: 5

Further more preferably the oligonucleotide is one of

UCAAUGACCACAUAGAUAAGGUCUC;   SEQ ID: 1

UACUCAUUAGUACUAUCGCUGCAGG;   SEQ ID: 2

UUAGAAUCAUUCUUGAUGUCUCUGG;   SEQ ID: 3

It is within the scope of the present invention to use siRNA where the sugar components of the oligonucleotides have been chemically modified.

According to a preferred aspect of the present invention there is provided a skin lightening composition comprising:

(a) an siRNA comprising an oligonulceotide comprising a sequence selected from the group consisting of

UCAAUGACCACAUAGAUAAGGUCUC;   SEQ ID: 1

UAACAGCCGGACAAGAAGAUGAUGG;   SEQ ID: 4

AAGAGGUUGAAGUUCUUGAAGAUGC;   SEQ ID: 5 and a portion comprising at least 19 nucleotides thereof; and (b) a cosmetically acceptable vehicle;

wherein the oligonucleotide size is from 19 to 30 nucleotides.

According to yet another preferred aspect of the present invention there is provided a skin lightening composition comprising:

(a) an siRNA comprising an oligonulceotide comprising a sequence selected from the group consisting of

UACUCAUUAGUACUAUCGCUGCAGG;   SEQ ID: 2

UUAGAAUCAUUCUUGAUGUCUCUGG;   SEQ ID: 3

UUUAUUAAAGAUGCCACGUGG;   SEQ ID: 7

UAGAAUCCCACCUUUACUCTG;   SEQ ID: 10 and a portion comprising at least 20 nucleotides thereof; and (b) a cosmetically acceptable vehicle;

wherein the oligonucleotide size is from 20 to 30 nucleotides.

In the above preferred aspect the oligonucleotide is at least 20 nucleotides long, preferably at least 22 more preferably at least 25 nucleotides long.

According to another aspect of the present invention there is provided a skin lightening composition comprising:

(a) an siRNA comprising an oligonulceotide comprising a sequence selected from the group consisting of

CAAUUCACCCACACUGUTC;   SEQ ID: 6

GUUCAUGAUGCCAAAGGCCTG;   SEQ ID: 8

UUCAUUGCUGUGAUCAUUCGC;   SEQ ID: 9 and a portion comprising at least 19 nucleotides thereof; and (b) a cosmetically acceptable vehicle selected from an emulsion, lotion, cream, foam, gel, soap bar, stick, mask, pad or patch;

wherein the oligonucleotide size is from 19 to 30 nucleotides.

The oligonucleotide is preferably present in a safer and effective amount in the composition to enable visible improvement in skin lightening efficacy. The oligonucleotide is more preferably present in 0.00001 to 1%, more preferably 0.0001 to 0.01% by weight of the composition.

The cosmetically acceptable vehicle is preferably an emulsion, lotion, cream, foam, gel, soap bar, stick, mask, pad or patch more preferably a cream, gel or lotion.

When the composition of the invention is a cream it preferably comprises 3 to 25% fatty acid. When the composition of the invention is a lotion it preferably comprises 1 to 20% fatty acid. A more preferred format is a cream, further more preferably a vanishing cream. Vanishing cream base is one which comprises 1 to 25%, more preferably 5 to 20% fatty acid. The fatty acids may be saturated or unsaturated fatty acids. The base preferably comprises 0.1 to 10%, more preferably 0.1 to 3% soap. $C_{12}$ to $C_{20}$ fatty acids are especially preferred in vanishing cream bases, further more preferred being $C_{14}$ to $C_{18}$ fatty acids. In creams, the fatty acid is preferably substantially a mixture of stearic acid and palmitic acid. Soaps in the vanishing cream base include alkali metal salt of fatty acids, like sodium or potassium salts The soap is preferably the potassium salt of the fatty acid mixture. The fatty acid in vanishing cream base is often prepared using hystric acid which is substantially (generally about 90 to 95%) a mixture of stearic acid and palmitic acid. Thus, inclusion of hystric acid and its soap to prepare the vanishing cream base is within the scope of the present invention. The cosmetically acceptable base is usually from 10 to 99.9%, preferably from 50 to 99% by weight of the composition. The cosmetically acceptable base preferably includes water. Water is preferably included in 35 to 90%, more preferably 50 to 85%, further more preferably 50 to 80% by weight of the composition.

The composition of the invention preferably comprises a UV-A and/or a UV-B sunscreen. Organic sunscreens of these two types are generally available from the following major groups: benzophenones, anthranilates, dibenzoylmethanes, salicylates, cinnamates, camphores, and triazins.

The composition of the invention preferably comprises a UV-A sunscreen which is a dibenzoylmethane or its derivative. The most preferred dibenzoylmethane derivative is 4-tert.-butyl-4'-methoxydibenzoylmethane.

An oil soluble UV-B organic sunscreen is preferably included in the composition of the invention. Oil soluble UV-B sunscreen is preferably selected from the class of cinnamic acid, salicylic acid, diphenyl acrylic acid or derivatives thereof. A few of the preferred oil soluble UV-B sunscreens which are commercially available and useful for inclusion in the composition of the invention are Octisalate™' Homosalate™, NeoHelipan™, Octocrylene™, Oxybenzone™ or Parsol MCX™. Alternately, a water soluble organic UVB sunscreen is preferably included in the composition of the invention. Preferred water soluble organic UVB sunscreen is Phenyl benzimidazole sulfonic acid.

The composition of the invention preferably comprises 0.1 to 5%, more preferably 0.2 to 5%, further more preferably 0.4 to 3%, by weight UV-A and/or UV-B sunscreen based on total weight of the composition and including all ranges subsumed therein.

Photostabilizers may be included in the composition of the present invention. Suitable photostabilising compounds are of the diphenylacrylate, benzylidene camphor, napthalate, triazine, fluorene or diarylbutadiene class.

Other useful sun-protective agents e.g. inorganic sunblocks may be preferably used in the present invention. These include, for example, zinc oxide, iron oxide, silica, such as fumed silica, or titanium dioxide. The total amount of sun block that is preferably incorporated in the composition according to the invention is from 0.1 to 5% by weight of the composition.

The composition of the invention may additionally comprise a skin lightening agent. The skin lightening agent is preferably chosen from a vitamin B3 compound or its derivative e.g. niacin, nicotinic acid, niacinamide or other well known skin lightening agents e.g. aloe extract, ammonium lactate, azelaic acid, kojic acid, citrate esters, ellagic acid, glycolic acid, green tea extract, hydroquinone, lemon extract, linoleic acid, magnesium ascorbyl phosphate, vitamins like vitamin B6, vitamin B12, vitamin C, vitamin A, a dicarboxylic acid, resorcinol derivatives, hydroxycarboxylic acid like lactic acid and their salts e.g. sodium lactate, and mixtures thereof. Vitamin B3 compound or its derivative e.g. niacin, nicotinic acid, niacinamide are the more preferred skin lightening agent as per the invention, most preferred being niacinamide. Niacinamide, when used, is preferably present in an amount in the range of 0.1 to 10%, more preferably 0.2 to 5% by weight of the composition.

The composition according to the invention may also comprise other diluents. The diluents act as a dispersant or carrier for other materials present in the composition, so as to facilitate their distribution when the composition is applied to the skin. Diluents other than water can include liquid or solid emollients, solvents, humectants, thickeners and powders.

The composition of the invention may comprise a conventional deodorant base as the cosmetically acceptable carrier. By a deodorant is meant a product in the stick, roll-on, or propellant medium which is used for personal deodorant benefit e.g. application in the under-arm or any other area which may or may not contain anti-perspirant actives.

Deodorant compositions can generally be in the form of firm solids, soft solids, gels, creams, and liquids and are dispensed using applicators appropriate to the physical characteristics of the composition.

The compositions of the present invention can comprise a wide range of other optional components. The CTFA Cosmetic Ingredient Handbook, Second Edition, 1992, which is incorporated by reference herein in its entirety, describes a wide variety of non-limiting cosmetic and pharmaceutical ingredients commonly used in the skin care industry, which are suitable for use in the compositions of the present invention. Examples include: antioxidants, binders, biological additives, buffering agents, colorants, thickeners, polymers, astringents, fragrance, humectants, opacifying agents, conditioners, exfoliating agents, pH adjusters, preservatives, natural extracts, essential oils, skin sensates, skin soothing agents, and skin healing agents.

According to another aspect of the present invention there is provided a method of lightening skin comprising the step of applying a skin lightening composition of the present invention on to a desired surface of the skin.

The composition of the invention is targeted for cosmetic and dermal applications and is therefore preferably not for therapeutic/medical use.

The invention is now further described by way of the following non-limiting examples.

EXAMPLES

Examples 1 to 10

Melanin Content Assay as a Quantification of the Efficacy of the siRNA Sequences for Skin Lightening Ten siRNA double strands of which one strand has the oligonucleotide as given below were synthetically prepared and used to estimate the potential as skin lightening agent using the melanin content in-vitro assay. It is clear to a person skilled in this area that specifying a single strand is sufficient to fully define the double stranded siRNA. The in-vitro assay was carried out as below:

siRNA Comprising the Following Oligonucleotide Sequences Assayed:

```
                                          SEQ ID: 1
    UCAAUGACCACAUAGAUAAGGUCUC;

SEQ ID: 2
    UACUCAUUAGUACUAUCGCUGCAGG;

SEQ ID: 3
    UUAGAAUCAUUCUUGAUGUCUCUGG;

SEQ ID: 4
    UAACAGCCGGACAAGAAGAUGAUGG;

SEQ ID: 5
    AAGAGGUUGAAGUUCUUGAAGAUGC;

SEQ ID: 6
    CAAUUCACCCACACUGUTC;

SEQ ID: 7
    UUUAUUAAAGAUGCCACGUGG;
```

-continued

GUUCAUGAUGCCAAAGGCCTG;  SEQ ID: 8

UUCAUUGCUGUGAUCAUUCGC;  SEQ ID: 9
or

UAGAAUCCCACCUUUACUCUG  SEQ ID: 10 siRNA Transfection

Primary human melanocytes were cultured for 24 hrs. Cells were transfected with Mirus Trans IT-TKO transfection reagent and duplex oligomers in culture media. Cells were incubated at 37° C. in a humidified $CO_2$ incubator and harvested post transfection 96-144 hours for melanin content and viability assay.

Viability:

After 96, 120, 144 or 168 hours of transfection, media was removed and neutral red (50 μg/ml in melanocyte culture media) was added to cells and incubated for 3 hours at 37° C. in $CO_2$ incubator. At the end of incubation, cells were washed with 1× phosphate buffer solution (PBS) and dye was extracted using desorption solution (ethanol: water: glacial acetic acid, 50:49:1) and absorbance was measured at 540 nm.

Melanin Content:

After 96, 120, 144 or 168 hours of transfection, media was removed and cells were solubilized in 200 μl of 10% DMSO in 1N NaOH. After 1 hour at 60° C., absorbance was measured at 400 nm.

Calculation:

Melanin content is expressed as % melanin content over scramble treated cells.

The experiments were carried out and the data on melanin content as a percentage of the control sample is summarized as an average of 3 readings in table 1. Kojic acid is known to complete action within 72 hours.

TABLE 1

| Example | Concentration (nM) | Time point (hours) | % control melanin | Std deviation |
|---|---|---|---|---|
| SEQ ID: 1 | 20 | 144 | 76 | 10 |
| SEQ ID: 2 | 20 | 144 | 75 | 3 |
| SEQ ID: 3 | 20 | 144 | 80 | 8 |
| SEQ ID: 4 | 20 | 96 | 62 | 1 |
| SEQ ID: 5 | 20 | 144 | 77 | 5 |
| SEQ ID: 6 | 50 | 168 | 81 | 4 |
| SEQ ID: 7 | 50 | 168 | 85 | 4 |
| SEQ ID: 8 | 20 | 144 | 81 | 8 |
| SEQ ID: 9 | 20 | 144 | 84 | 15 |
| SEQ ID: 10 | 10 | 120 | 83 | 5 |
| Kojic acid (control) | $10^5$ | 72 | 76 | 7 |

The data in table 1 indicates that compositions of the invention (SEQ ID:1 to SEQ ID:10) provides good melanin content reduction, comparable to one of the best known active viz. kojic acid. The advantage of the invention is that the siRNA can be used at a concentration that is orders of magnitude lower than the chemical active.

The invention claimed is:

1. A method of lightening skin comprising the step of applying on to a desired surface of the skin a skin lightening composition comprising:
   (a) an siRNA comprising an oligonucleotide comprising a sequence selected from the group consisting of

UCAAUGACCACAUAGAUAAGGUCUC; SEQ ID: 1

UACUCAUUAGUACUAUCGCUGCAGG; SEQ ID: 2

UUAGAAUCAUUCUUGAUGUCUCUGG; SEQ ID: 3

UAACAGCCGGACAAGAAGAUGAUGG; SEQ ID: 4

AAGAGGUUGAAGUUCUUGAAGAUGC; SEQ ID: 5

CAAUUCACCCACACUGUTC; SEQ ID: 6

UUUAUUAAAGAUGCCACGUGG; SEQ ID: 7

UAGAAUCCCACCUUUACUCTG; SEQ ID: 10 and
   a portion comprising at least 19 nucleotides thereof; and
   (b) a cosmetically acceptable vehicle;
   wherein the oligonucleotide has a function to suppress an expression of a gene corresponding to a receptor selected from the group of receptors consisting of: c-Kit Tyrosine kinase receptor, Endothelin receptor A (ED-NRA), Endothelin receptor B (EDNRB), Melanocortin 1 receptor, and Frizzled 1 (Fz1) receptor; and
   wherein a size of the oligonucleotide is from 19 to 30 nucleotides.

2. A skin lightening composition comprising:
   (a1) a first siRNA comprising an oligonucleotide comprising a first sequence selected from the group consisting of

UCAAUGACCACAUAGAUAAGGUCUC; SEQ ID: 1

UAACAGCCGGACAAGAAGAUGAUGG; SEQ ID: 4

AAGAGGUUGAAGUUCUUGAAGAUGC; SEQ ID: 5 and
   a first portion comprising at least 19 nucleotides thereof; wherein a size of the oligonucleotide is from 19 to 30 nucleotides; or
   (a2) a second siRNA comprising an oligonucleotide comprising a second sequence selected from the group consisting of

UACUCAUUAGUACUAUCGCUGCAGG; SEQ ID: 2

UUAGAAUCAUUCUUGAUGUCUCUGG; SEQ IDf: 3

UUUAUUAAAGAUGCCACGUGG; SEQ ID: 7

UAGAAUCCCACCUUUACUCTG; SEQ ID: 10 and
   a second portion comprising at least 20 nucleotides thereof;
   wherein the size of the oligonucleotide is from 20 to 30 nucleotides;
   wherein the oligonucleotide has a function to suppress an expression of a gene corresponding to a receptor selected from the group of receptors consisting of: c-Kit Tyrosine kinase receptor, Endothelin receptor A (ED-NRA), Endothelin receptor B (EDNRB), Melanocortin 1 receptor, and Frizzled 1 (Fz1) receptor; and
   (b) a cosmetically acceptable vehicle.

3. The skin lightening composition as claimed in claim 2 wherein the cosmetically acceptable vehicle is a cream, gel or lotion.

4. The skin lightening composition as claimed in claim 3 wherein the first siRNA or the second siRNA is present in 0.00001 to 1% by weight of the composition.

* * * * *

SEQUENCE LISTING

```
<160> NUMBER OF SEQ ID NOS: 10

<210> SEQ ID NO 1
<211> LENGTH: 25
<212> TYPE: RNA
<213> ORGANISM: Artificial Secuence
<220> FEATURE:
<223> OTHER INFORMATION: siRNA Oligonucleotide sequence

<400> SEQUENCE: 1
ucaaugacca cauagauaag gucuc                                       25

<210> SEQ ID NO 2
<211> LENGTH: 25
<212> TYPE: RNA
<213> ORGANISM: >  Artificial Sequence

<400> SEQUENCE: 2
ucaaugacca cauagauaag gucuc                                       25

<210> SEQ ID NO 3
<211> LENGTH: 25
<212> TYPE: RNA
<213> ORGANISM: Artifical Sequence

<400> SEQUENCE: 3
uuagaaucau ucuugauguc ucugg                                       25

<210> SEQ ID NO 4
<211> LENGTH: 25
<212> TYPE: RNA
<213> ORGANISM: Artificial Sequence
<220> FEATURE:
<223> OTHER INFORMATION: si
```

-continued

<400> SEQUENCE: 4
uaacagccgg acaagaagau gaugg                                   25

<210> SEQ ID NO 5
<211> LENGTH: 25
<212> TYPE: RNA
<213> ORGANISM: Artificial Sequence
<220> FEATURE:
<223> OTHER INFORMATION: siRNA oligonucleotide sequence

<400> SEQUENCE: 5
aagagguuga aguucuugaa gaugc                                   25

<210> SEQ ID NO 6
<211> LENGTH: 19
<212> TYPE: DNA
<213> ORGANISM: Artificial Sequence
<220> FEATURE:
<223> OTHER INFORMATION: siRNA oligonucleotide sequence

<400> SEQUENCE: 6
caauucaccc acacugutc                                          19

<210> SEQ ID NO 7
<211> LENGTH: 21
<212> TYPE: RNA
<213> ORGANISM: Artificial Sequence
<220> FEATURE:
<223> OTHER INFORMATION: siRNA oligonucleotide sequence

<400> SEQUENCE: 7
uuuauuaaag augccacgug g                                       21

<210> SEQ ID NO 8
<211> LENGTH: 21
<212> TYPE: DNA
<213> ORGANISM: Artificial Sequence
<220> FEATURE:
<223> OTHER INFORMATION: siRNA oligonucleotide sequence

<400> SEQUENCE: 8
guucaugaug ccaaaggcct g                                       21

<210> SEQ ID NO 9
<211> LENGTH: 21
<212> TYPE: RNA
<213> ORGANISM: Artificial Sequence
<220> FEATURE:
<223> OTHER INFORMATION: siRNA oligonucleotide sequence

<400> SEQUENCE: 9
uucauugcug ugaucauucg c                                       21

<210> SEQ ID NO 10
<211> LENGTH: 21
<212> TYPE: DNA
<213> ORGANISM: Artificial Sequence
<220> FEATURE:
<223> OTHER INFORMATION: siRNA oligonucleotide sequence

<400> SEQUENCE: 10
uagaauccca ccuuuacuct g                                       21